(12) United States Patent
Rink et al.

(10) Patent No.: US 6,515,192 B1
(45) Date of Patent: Feb. 4, 2003

(54) HYPERBRANCHED COMPOUNDS WITH A TETRAFUNCTIONAL CENTRAL GROUP AND USE OF SAME

(75) Inventors: Heinz-Peter Rink, Münster (DE); Dunja Mikolajetz, Münster (DE)

(73) Assignee: BASF Coatings AG, Muenster-Hiltrup (DE)

( * ) Notice: Subject to any disclaimer, the term of this patent is extended or adjusted under 35 U.S.C. 154(b) by 0 days.

(21) Appl. No.: 09/763,279

(22) PCT Filed: Aug. 18, 1999

(86) PCT No.: PCT/EP99/06042

§ 371 (c)(1), (2), (4) Date: Feb. 20, 2001

(87) PCT Pub. No.: WO00/14049

PCT Pub. Date: Mar. 16, 2000

(30) Foreign Application Priority Data

Sep. 5, 1998 (DE) .......................... 198 40 605

(51) Int. Cl.$^7$ ...................... C07C 69/003; C08G 85/00; C04D 201/00; C04J 201/00
(52) U.S. Cl. ............................ 585/16; 106/316; 260/1; 524/80
(58) Field of Search ............................ 260/1; 106/316; 524/80; 585/16

(56) References Cited

U.S. PATENT DOCUMENTS

| | | | |
|---|---|---|---|
| 4,710,542 A | 12/1987 | Forgione et al. ............. | 525/127 |
| 4,939,213 A | 7/1990 | Jacobs, III et al. ......... | 525/329.9 |
| 5,084,541 A | 1/1992 | Jacobs, III et al. ........... | 528/45 |
| 5,136,014 A | 8/1992 | Figuly ........................ | 528/272 |
| 5,288,865 A | 2/1994 | Gupta ........................ | 544/200 |
| 5,475,073 A | 12/1995 | Guo ........................... | 526/333 |
| 5,480,493 A | 1/1996 | Harry, Jr. ..................... | 134/4 |
| 5,534,598 A | 7/1996 | Guo ........................... | 525/329.2 |

FOREIGN PATENT DOCUMENTS

| | | | | |
|---|---|---|---|---|
| DE | 44 01 544 A1 | 1/1994 | ........... | C08G/18/32 |
| DE | 195 34 361 A1 | 9/1995 | ......... | C09D/175/14 |
| EP | 0 245 700 A2 | 4/1987 | ......... | C07D/251/54 |
| EP | 0 604 922 A1 | 12/1993 | ......... | C08K/5/3492 |
| EP | 0 708 788 B1 | 6/1994 | ........... | C08G/18/08 |
| EP | 0 767 185 A1 | 6/1995 | ......... | C08F/212/06 |
| EP | 0 743 335 A2 | 11/1996 | ......... | C08G/63/685 |
| WO | WO 93/17060 | 9/1993 | ........... | C08G/63/02 |
| WO | WO 9317060 A1 * | 9/1993 | ........... | C08G/63/02 |
| WO | WO 9612754 A1 * | 5/1996 | ........... | C08G/63/20 |
| WO | WO 96/12754 | 5/1996 | ........... | C08G/63/20 |

\* cited by examiner

Primary Examiner—David W. Wu
Assistant Examiner—Kelechhi Egwim

(57) ABSTRACT

Hyperbranched compounds having a tetrafunctional central group of the general formula I $$C[-A_q-X-]_m[-A_r-X-]_n[-A_s-X-]_o[-A_t-X-]_p \quad (I),$$

in which the indices and variables have the following meanings:

$m+n+o+p=4$; where m=an integer from 1 to 3 and n, o and p=0 or an integer from 1 to 3;

q,r,s and t=an integer from 1 to 5, where q>r, s and t;

X=—O—, —S— or —NH—;

A=—CR$_2$—; where
R=—H, —F, —Cl, —Br, —CN, —NO$_2$, C$_1$–C$_3$ alkyl or C$_1$–C$_3$ haloalkyl or C$_1$–C$_3$ alkoxy radical or, if q, r, s and/or t=at least 2, a C$_2$–C$_4$ alkanediyl and/or C$_2$–C$_4$ oxaalkanediyl radical which bridges 2 to 5 carbon atoms, and/or an oxygen atom —O—, which bridges 3 to 5 carbon atoms, of the radical —A—.

19 Claims, No Drawings

HYPERBRANCHED COMPOUNDS WITH A TETRAFUNCTIONAL CENTRAL GROUP AND USE OF SAME

The present invention relates to a novel hyperbranched compound having a tetrafunctional central group. The present invention additionally relates to a novel process for preparing hyperbranched compounds. The present invention further relates to the use of the novel hyperbranched compound as a functional component in multisubstance mixtures and for preparing dendrimers of higher generations.

Hyperbranched compounds and dendrimers containing a tetrafunctional central group are known from the patent WO 93/17060. The central group used is a tetrol such as pentaerythritol, ditrimethylolpropane, diglycerol and ditrimethylolethane. However, the corresponding hyperbranched compounds are too viscous and too poorly soluble for numerous end uses. For example, it is impossible to prepare particularly high-solids coating compositions, adhesives or sealing compounds in solution or dispersion in aqueous or organic media using the known hyperbranched compounds. Additionally, the liquid coating compositions, adhesives or sealing compounds which comprise the known hyperbranched compounds as functional components are too viscous for the majority of application technologies. Accordingly, powder coating materials and powder slurries comprising known hyperbranched compounds have film formation temperatures which in many cases are too close to the crosslinking temperature.

It is an object of the present invention to find novel hyperbranched compounds which no longer have the disadvantages of the prior art and which make it possible to prepare new coating compositions, adhesives and sealing compounds which have advantageously low viscosities even at high solids content or in the melt. A further object of the present invention is to find a novel process for preparing hyperbranched compounds which allows such compounds to be obtained in a particularly simple way. Another object of the present invention is to find novel end uses for hyperbranched compounds, especially as functional components in multisubstance mixtures and for preparing dendrimers of higher generations.

Accordingly, we have found the novel hyperbranched compounds having a tetrafunctional central group of the general formula I

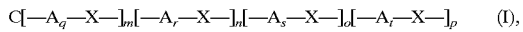     (I), in which the indices and variables have the following meanings:

$m+n+o+p=4$; where m=an integer from 1 to 3 and n, o and p=0 or an integer from 1 to 3;

q, r, s and t=an integer from 1 to 5, where q>r, s, t;

X=—O—, —S— or —NH—;

A=—CR$_2$—; where

R=—H, —F, —Cl, —Br, —CN, —NO$_2$, C$_1$–C$_3$ alkyl or C$_1$–C$_3$ haloalkyl or C$_1$–C$_3$ alkoxy radical or, if q, r, s and/or t=at least 2, a C$_2$–C$_4$ alkanediyl and/or C$_2$–C$_4$ oxaalkanediyl radical which bridges 2 to 5 carbon atoms, and/or an oxygen atom —O—, which bridges 3 to 5 carbon atoms, of the radical —A—.

In the text below, the novel hyperbranched compounds having a tetrafunctional central group of the general formula I are referred to for brevity as "compounds of the invention".

The tetrafunctional central groups of the general formula I are referred to below for brevity as "central groups I".

Accordingly, the novel process for preparing the compounds of the invention is referred to below as the "process of the invention".

Similarly, in the text below, the novel multisubstance mixtures which comprise the compounds of the invention are referred to as "multisubstance mixtures of the invention", in particular as "coating compositions of the invention", "adhesives of the invention", or "sealing compounds of the invention".

The novel dendrimers of higher generations which can be prepared using the compounds of the invention are referred to below as "dendrimers of the invention"

In the light of the prior art it is surprising that the object of the present invention was able to be achieved with the aid of the compounds of the invention. In particular, it was not expected that varying the central group, sometimes referred to as an initiator group in the prior art, would have such far-reaching technical consequences.

The essential constituent of the compounds of the invention is the central group I.

In the general formula I, the indices m, n, o and p add up to 4. The index m is always larger than 0 and stands for an integer from 1 to 3, in particular 1.

While observing the above boundary condition, the indices n, o and p have the value 0 or represent an integer from 1 to 3. This means that it is not possible for each of these indices to adopt the value 0.

In accordance with the invention, the following combinations of values in the indices are of advantage:

m=1 and n, o, p=1;

m=1, n=2, o, p=1;

m=1, n=2, o=1 and p=0;

m=1, n=3, o, p=0;

m=2, n=1, o=1 and p=0;

m=2, n=2 and o, p=0;

m=3, n=1 and o, p=0.

Of these, particular advantage is possessed by those numerical combinations in which m=1.

In the general formula I, the indices q, r, s and t denote integers from 1 to 5. In this case the index q is always larger than the indices r, s and t. Accordingly, the index q has a value of at least 2.

In accordance with the invention, the following numerical combinations of the indices are of advantage:

q=2, r, s and/or t=1;

q=3, r, s and/or t=1 and/or 2;

q=4, r, s and/or t=1, 2 and/or 3;

q=5, r, s and/or t=1, 2, 3 and/or 4.

The variable —X— in the general formula I denotes divalent oxygen atoms —O— or sulfur atoms —S— or a secondary amino group —NH—. In accordance with the invention it is advantageous if —X— is —O—.

The variable —A— in the formula I denotes a divalent radical —CR$_2$—.

The radical R therein represents hydrogen atoms —H, fluorine atoms —F, chlorine atoms —Cl, bromine atoms —Br, nitrile groups —CN, nitro groups —NO$_2$, C$_1$–C$_3$ alkyl or C$_1$–C$_3$ haloalkyl groups or C$_1$–C$_3$ alkoxy groups. Examples of suitable groups of this kind are methyl, ethyl, propyl, trifluoromethyl, trichloromethyl, perfluoroethyl, perfluoropropyl, methoxy, ethoxy or propoxy groups.

Of advantage in accordance with the invention are hydrogen atoms or methyl groups, which are therefore used for preference. In particular, hydrogen atoms are used. Accordingly, the variables —A— particularly preferred in accordance with the invention comprise methylene groups.

If in the general formula I at least one of the indices q, r, s and/or t represents at least the number 2, the radical R may also represent a $C_2$–$C_4$ alkanediyl radical and/or oxaalkanediyl radical which cyclically bridges from 2 to 5 carbon atoms of the radical —A—. Alternatively, the radical —R— may represent an oxygen atom —O— which cyclically bridges from 3 to 5 carbon atoms of the radical —A—. Formed as a result are cyclopentane-1,2- or 1,3-diyl groups, tetrahydrofuran-2,3-, -2,4-, -2,5- or -3,4-diyl groups, cyclohexane-1,2-, -1,3- or -1,4-diyl groups, or tetrahydropyran-2,3-, -2,4-, -2,5- or -2,6-diyl groups, but not epoxide groups.

Examples of central groups I which are especially advantageous in accordance with the invention are derived formally, therefore, from the tetrols (III1) to (III10) described below by abstracting the four hydrogen atoms of the hydroxyl groups.

Of these, the central group I which derives from the tetrol (III1) (2,2-bishydroxymethyl-1,4-butanediol; homopentaerythritol) is very particularly advantageous and is therefore used with very particular preference in accordance with the invention.

In the compounds of the invention, the above-described variables —X— are connected by way of spacer groups to in each case one reactive functional group. In the context of the present invention, the term "reactive functional group" refers to a group which, in contrast to an inert group, is readily available for further reactions. Accordingly, the group in question may comprise any desired group known from organic chemistry. In accordance with the invention, however, it is of advantage if it comprises a group of the general formula II.

—X—B    (II)

In the general formula II, the variable —X— represents divalent oxygen and sulfur atoms or secondary amino groups. In accordance with the invention it is of advantage if the variable —X— represents divalent oxygen atoms.

In the general formula II, the variable B represents a hydrogen atom —H, a group —Z or a linear or branched group —$R^1$—(—$Z^1$)$_u$, in which the index u=1 or 2.

Suitable groups —Z include all reactive functional groups of organic chemistry which under the customary and known conditions enter into reactions which lead to the desired further buildup of the compound of the invention or to its linking with other compounds, such as, for instance, with the crosslinkers known from the coating compositions or the adhesives. Examples of groups —Z which are particularly advantageous in accordance with the invention are:

—C(O)—NH$_2$,
—C(O)—NH—C(O)—NH$_2$,
—C(O)—OR$^2$,
—C(O)—NH—C(O)—OR$^2$,
—C(O)—CH$_2$—C(O)—R$^2$
—C(O)—CH$_2$—C(O)—OR$^2$
—C(O)—CR$^3$=CH$_2$,

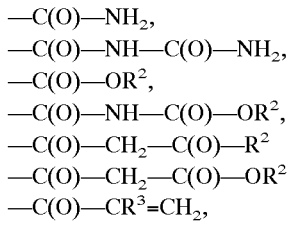

—Si—(OR$^4$)$_3$,

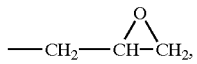
—C(O)—(—CH$_2$—)$_v$—CH=CH$_2$; in which the index v is 0 or is an integer from 1 to 3;
—C(O)—CH=CH—C(O)—O—R$^2$,
—C(O)—CH=CH—CH=CH—R$^2$ and
—C(O)—CH=CH—CH$_2$—CH=CH—R$^2$.

In these formulae, the radicals R$^2$ designate unsubstituted or substituted $C_1$–$C_{10}$ alkyl, $C_5$–$C_{10}$ cycloalkyl, $C_6$–$C_{20}$ cycloalkylalkyl, $C_6$–$C_{20}$ alkylcycloalkyl, $C_6$–$C_{10}$ aryl, $C_7$–$C_{20}$ arylalkyl, $C_7$–$C_{20}$ alkylaryl, $C_{11}$–$C_{26}$ arylcycloalkyl or $C_{11}$–$C_{26}$ cycloalkylaryl radical, the alkyl radicals being branched or unbranched.

Suitable substituents for these radicals R$^2$ are all organic radicals which are substantially inert, i.e., which do not enter into reactions with the compounds which are used for the buildup of the compounds of the invention or for their further reaction. Examples of suitable inert organic radicals are halogen atoms, nitro groups, nitrile groups or alkoxy groups.

Examples of suitable unsubstituted or substituted $C_1$–$C_{10}$ alkyl radicals for use in accordance with the invention are methyl, ethyl, propyl, butyl, pentyl, hexyl, heptyl, octyl, nonyl or decyl radicals, of which the methyl, ethyl and propyl radicals are particularly advantageous and are therefore used with preference.

Examples of suitable unsubstituted or substituted $C_5$–$C_{10}$ cycloalkyl radicals for use in accordance with the invention are cyclopentyl, cyclohexyl, cycloheptyl, cyclooctyl or decalinyl radicals, of which the cyclopentyl and cyclohexyl radicals are advantageous and are therefore used with preference.

Examples of suitable unsubstituted or substituted $C_6$–$C_{20}$ cycloalkylalkyl radicals for use in accordance with the invention are cyclopentylmethyl, cyclopentylethyl, cyclohexylmethyl, cyclohexylethyl or cyclohexylpropyl radicals, of which the cyclohexylmethyl radical is advantageous and is therefore used with preference.

Examples of suitable unsubstituted or substituted $C_6$–$C_{20}$ alkylcycloalkyl radicals for use in accordance with the invention are 4-methylcyclohex-1-yl, 2-ethyl-cyclohex-1-yl or 4-methyl-2-ethylcyclohex-1-yl, of which the 4-methylcyclohex-1-yl radical is advantageous and is therefore used with preference.

Examples of suitable unsubstituted or substituted $C_6$–$C_{10}$ aryl radicals for use in accordance with the invention are phenyl or naphthyl radicals, of which the phenyl radicals are advantageous and are therefore used with preference.

Examples of suitable unsubstituted or substituted $C_7$–$C_{20}$ arylalkyl radicals for use in accordance with the invention are phenylmethyl, 2-phenylethyl or 3-phenylpropyl radicals, of which the 2-phenylethyl radicals are advantageous and are therefore used with preference.

Examples of suitable unsubstituted or substituted $C_7$–$C_{20}$ alkylaryl radicals for use in accordance with the invention are 2-, 3- and 4-methylphen-1-yl, 4-butylphen-1-yl, 4-butyl-2-methylphen-1-yl, 2,4-di-methylphen-1-yl or 4-octylphen-1-yl radicals, of which the 4-butylphen-1-yl or 4-octylphen-1-yl radicals are advantageous and are therefore used with preference.

Examples of suitable $C_{11}$–$C_{26}$ arylcycloalkyl radicals for use in accordance with the invention are 2- or 3-phenylcyclopent-1-yl or 2-, 3- or 4-phenylcyclohex-1-yl radicals, of which the 4-phenylcyclohex-1-yl radical is advantageous and is therefore used with preference.

Examples of suitable $C_{11}$–$C_{26}$ cycloalkylaryl radicals for use in accordance with the invention are 2-, 3- or 4-cyclopentylphen-1-yl or 2-, 3- or 4-cyclohexylphen-1-yl radicals, of which the 4-cyclohexylphen-1-yl radical is advantageous and is therefore used with preference.

The radicals $R^3$ denote $C_1$–$C_4$-alkyl radicals or nitrile groups —CN. Examples of suitable $C_1$–$C_4$ alkyl radicals for use in accordance with the invention are methyl, ethyl, propyl or butyl radicals, of which the methyl radical is advantageous and is therefore used with preference.

The radicals $R^4$ denote unsubstituted or substituted $C_1$–$C_4$ alkyl radicals; examples of suitable alkyl radicals of this type for use in accordance with the invention are those mentioned above. Examples of suitable substituents for use in accordance with the invention are those listed above in connection with the radicals $R^2$.

The radical $R^1$ of the linear or branched group —$R^1$—(—$Z^1$)$_u$, in which the index u=1 or 2, comprises a divalent or trivalent radical which is derived from the following compounds:

(i) an alkane, alkene, cycloalkane, cycloalkene, alkylcycloalkane, alkylcycloalkene, alkenylcycloalkane, or alkenylcycloalkene, aromatics and heteroaromatics, and also an alkyl-, alkenyl-, cycloalkyl-, cycloalkenyl-, alkyl-cycloalkyl-, alkylcycloalkenyl-, alkenylcyclo alkyl- or alkenylcycloalkenyl-substituted aromatics or heteroaromatics; or ii) an abovementioned radical which contains at least one heteroatom in the chain and/or in the ring; or (iii) a radical mentioned under (i) or (ii) whose chain and/or ring is substituted.

Examples of suitable radicals $R^1$ for use in accordance with the invention are the radicals (i1) to (iii2) listed below, of which the radicals (i2) to (i5) and also (i20) and (i21) are advantageous and are therefore used with particular preference.

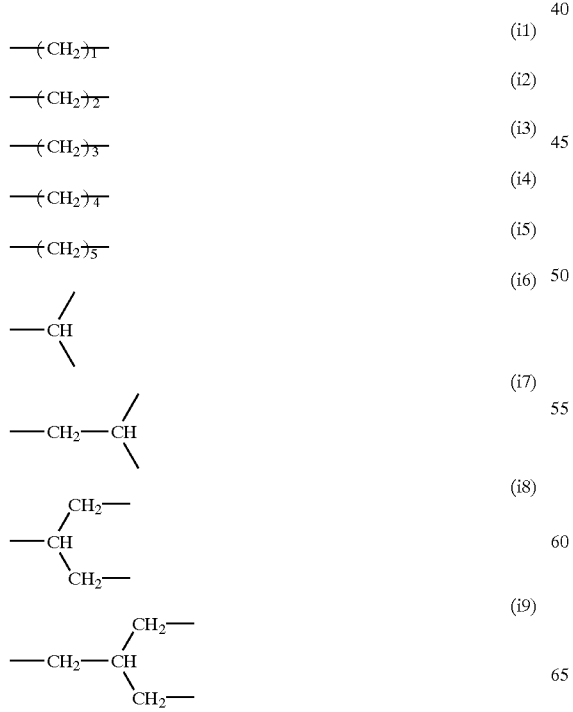

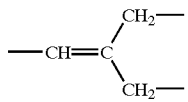
(i10)

(i11)

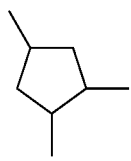
(i12)

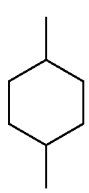
(i13)

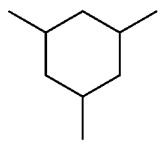
(i14)

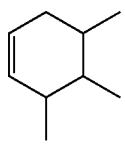
(i15)

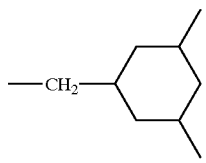
(i16)

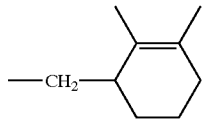
(i17)

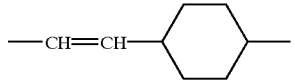
(i18)

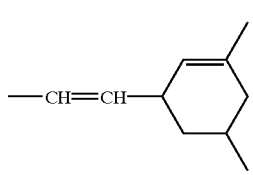
(i19)

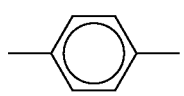
(i20)

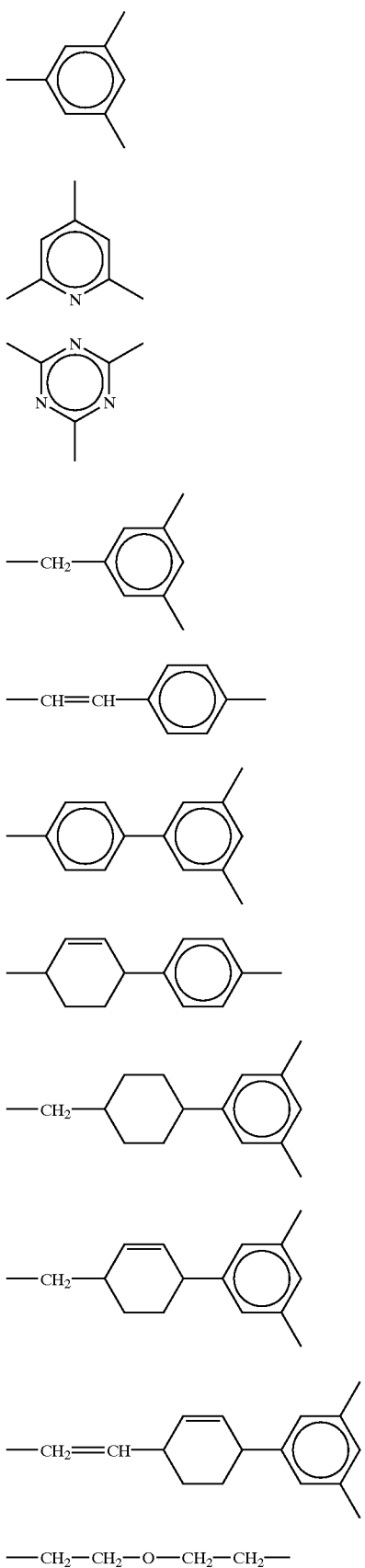
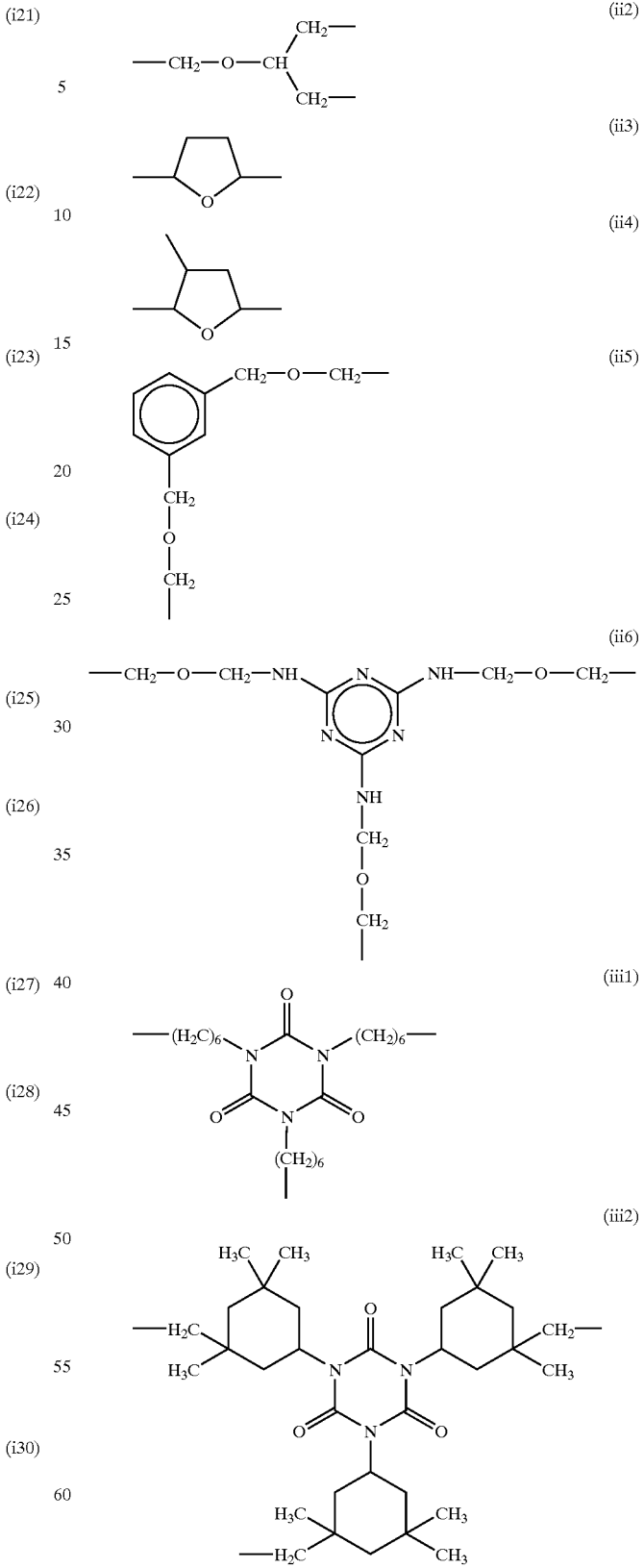
Examples of suitable substituents for use in accordance with the invention for the radicals $R^1$ are those listed above in connection with the radicals $R^2$.

As the variable $Z^1$ of the linear or branched group —$R^1$—(—$Z^1$)$_u$, in which the index u=1 or 2, suitable groups include all reactive functional groups of organic chemistry which under the customary and known conditions enter into reactions which lead to the desired further buildup of the compound of the invention or to its linking with other compounds, such as, for instance, with the crosslinkers known from the coating compositions or the adhesives. Examples of groups —$Z^1$ which are particularly advantageous in accordance with the invention are:

—OH, —NH$_2$, —SH,
—COOH, —SO$_3$H, —PO$_3$H
—O—C(O)—NH$_2$,
—O—C(O)—NH—C(O)—NH$_2$,
—NCO;
—NH—C(O)—OR$^2$,
—NH—C(O)—NH—C(O)—OR$^2$,
—O—C(O)—CH$_2$—C(O)—R$^2$,
—O—C(O)—CH$_2$—C(O)—OR$^2$
—O—C(O)—CR$^3$=CH$_2$;

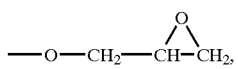

—O—Si—(OR$^4$)$_3$,
—O—(—CH$_2$—)$_v$—CH=CH$_2$ and
—O—C(O)—(—CH$_2$—)$_v$—CH=CH$_2$; in which the index v is 0 or an integer from 1 to 3, but in particular 0 and 1;
—O—C(O)—CH=CH—C(O)—O—R$^2$,
—O—C(O)—CH=CH—CH=CH—R$^2$ and
—O—C(O)—CH=CH—CH$_2$—CH=CH—R$^2$.

The reactive functional groups of the general formula II that are described in detail above are, in accordance with the invention, connected to the central group I by way of spacer groups.

Suitable spacer groups in accordance with the invention are all divalent organic radicals.

Examples of highly suitable divalent organic radicals are the divalent radicals $R^1$ described above, but especially the radical (i5).

Further examples of highly suitable divalent organic radicals for use in accordance with the invention are the spacer groups (iv1) to (iv8) listed below. Regarding their preparability and the advantageous properties which they impart to the compounds of the invention, these spacer groups have particular advantages, and so are used with preference. Of the spacer groups (iv1) to (iv8), the spacer groups (iv1) and (iv7) are especially advantageous and are therefore used with very particular preference.

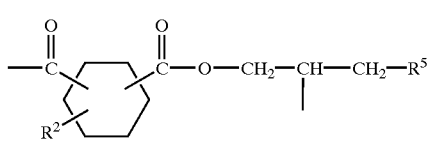

(IVA)

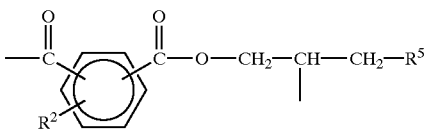

(IVB)

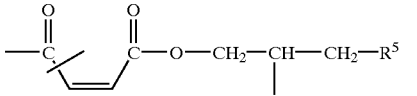

(iv7)

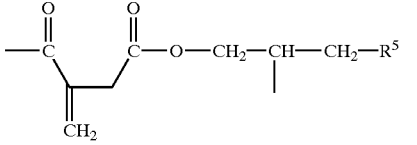

(iv8)

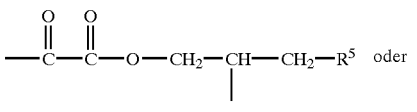

(iv9)

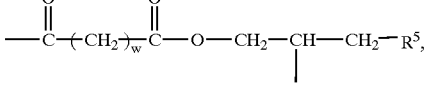

oder (iv10)

in which the index w=an integer from 1 to 10.

In the general formulae IVA and IVB, the radical $R^2$ is as defined above. The carbonyloxy substituents of the rings in the general formulae IVA are positioned 1,2 (spacer group iv1), 1,3 (spacer group iv2) or 1,4 (spacer group iv3) with respect to one another. The carbonyloxy substituents of the rings in the general formulae IVB are likewise positioned 1,2 (spacer group iv4), 1,3 (spacer group iv5) or 1,4 (spacer group iv6) with respect to one another.

In the formulae of the spacer groups (iv1) to (iv10) the radical $R^5$ denotes alkyl, cycloalkyl or aryl ether or alkyloxy, cycloalkyloxy or arylcarbonyloxy radicals, but especially tertiary alkylcarbonyloxy radicals. Particular examples of suitable radicals $R^5$ for use in accordance with the invention are Versatic$^R$ acid radicals, i.e., radicals of tertiary, highly branched monocarboxylic acids.

In accordance with the invention, the reactive functional group II described in detail above is linked with the spacer groups (iv1) to (iv10) by way of the secondary carbon atom.

The especially advantageous compounds of the invention have the particular advantage that their hydroxyl groups may be converted into other reactive functional groups II in an extraordinary variety of ways. Examples of such reactive functional groups II are the above-described groups —Z. They may be prepared, for example, by reacting the hydroxyl groups with the following compounds:

$R^2$O—C(O)—NH$_2$,
$R^2$O—C(O)—NH—C(O)—NH$_2$,
Cl—C(O)—OR$^2$,
Cl—C(O)—NH—C(O)—OR$^2$,
Cl—C(O)—CH$_2$—C(O)—R$^2$

Cl—C(O)—CH$_2$—C(O)—OR$^2$
HO—C(O)—CR$^3$=CH$_2$,

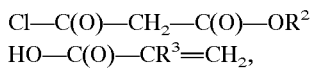

Cl—Si—(OR$^4$)$_3$,
Cl—(—CH$_2$—)$_v$—CH=CH$_2$ and
Cl—C(O)—(—CH$_2$—)$_v$—CH=CH$_2$; in which the index v is 0 or is an integer from 1 to 3, but in particular is 0 and 1;
Cl—C(O)—CH=CH—C(O)—O—R$^2$,
Cl—C(O)—CH=CH—CH=CH—R$^2$ and
Cl—C(O)—CH=CH—CH$_2$—CH=CH—R$^2$.

In these formulae, the indices and the variables are as defined above.

Moreover, the especially advantageous compounds of the invention which contain the spacer groups (iv7) and (iv8) have the very particular advantage that they can be modified on their olefinic double bond, so that besides the reactive functional groups II they may also contain further reactive functional groups. One example of such a modification is the addition of amines onto the double bonds.

Examples of especially advantageous compounds of the invention are, accordingly, the compounds (I1) to (I3).

skilled worker is therefore easily able to select suitable starting compounds based on the desired structures of the compounds of the invention.

It is substantial to the invention to prepare the central group I or the compound of the invention using a tetrafunctional compound of the general formula III C[—A$_q$—XH]$_m$[—A$_r$—XH]$_n$[—A$_s$—XH]$_o$[—A$_t$—XH]$_p$    (III).

In the text below, this compound is referred to for brevity as "compound III".

In the general formula III, the indices and variables are as defined above for the general formula I. In accordance with the invention it is of particular advantage if the variable X represents an oxygen atom —O—.

Accordingly, the tetrols of the general formula III are of particular advantage, and are therefore used with particular preference, for the preparation of the central group I and, respectively, of the compounds of the invention. In the text below these tetrols are referred to for brevity as "tetrols III".

Examples of especially suitable tetrols III for use in accordance with the invention are the tetrols (III1) to (III10):

HO—(—CH$_2$—)$_2$—C(—CH$_2$—OH)$_3$, (III1)
HO—(—CH$_2$—)$_3$—C(—CH$_2$—OH)$_3$, (III2)
HO—(—CH$_2$—)$_4$—C(—CH$_2$—OH)$_3$, (III3)
HO—(—CH$_2$—)$_5$—C(—CH$_2$—OH)$_3$, (III4)
[HO—(—CH$_2$—)$_2$—]$_2$C(CH$_2$—OH)$_2$, (III5)

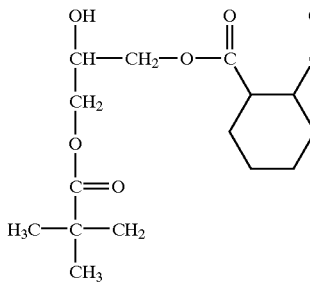
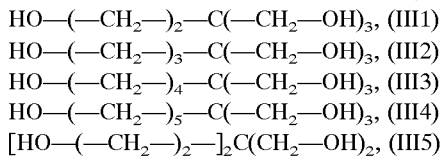
(I1)

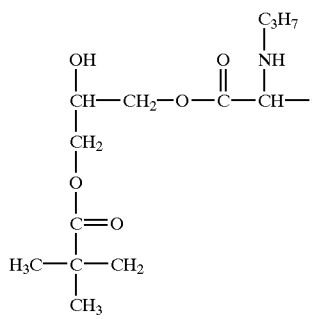
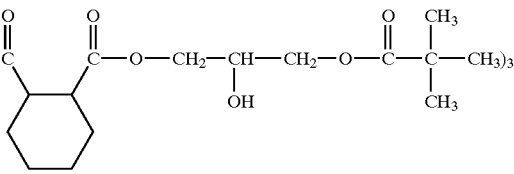
(I2)

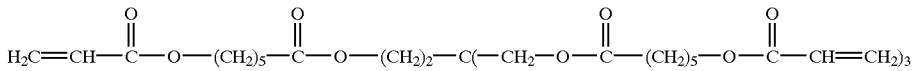
(I3)

The compounds of the invention may be prepared by the customary and known methods of preparing hyperbranched and dendrimeric compounds. Suitable synthesis methods are described, for example, in the patents WO 93/17060 or WO 96/12754 or in the book by G. R. Newkome, C. N. Moorefield and F. Vögtle, "Dendritic Molecules, Concepts, Syntheses, Perspectives", VCH, Weinheim, N.Y., 1996. The

[HO—(—CH$_2$—)$_2$—]$_3$C—CH$_2$—OH, (III6)
HO—(—CH$_2$—)$_3$—C[—(—CH$_2$—)$_2$—OH]$_3$, (III7)
HO—(—CH$_2$—)$_3$—C[—(—CH$_2$—)$_2$—OH]$_2$(—H$_2$—OH), (III8)
HO—(—CH$_2$—)$_4$—C(—CH$_2$—OH)[—(—CH$_2$—)$_2$—OH][—(—CH$_2$—)$_3$—OH] or (III9)

HO—(—CH$_2$—)$_5$—C(—CH$_2$—OH)[—(—CH$_2$—)$_4$—OH]2 (III10).

Of these, particular attention is drawn to the tetrol (III1) (2,2-bishydroxymethyl-1,4-butanediol; homopentaerythritol), since it imbues the compounds of the invention with especially advantageous properties. It is therefore used with very particular preference.

In accordance with a first variant, the procedure of the invention results in the reactive functional groups II and thus the compounds of the invention from the reaction of the compounds III, in particular the tetrols III, with suitable organic compounds in one stage.

Suitable organic compounds are all compounds which first carry functional groups which are able to react with the groups -XH described in detail above and second introduce the divalent radicals $R^1$ described in detail above into the intermediate.

Examples of suitable organic compounds for use in accordance with the invention are, accordingly, the divalent radicals $R^1$ described in detail above which carry, in particular, the following functional groups:

—NCO,
—Cl,
—Br,
—C(O)—Cl,
—C(O)—Br,
—C(O)—OH or
—C(O)—O—C(O)—.

Of these, the carboxyl groups and the anhydride groups are of particular advantage and are therefore used with particular preference.

It is therefore simple for the skilled worker to select the appropriate organic compounds for use in accordance with the invention on the basis of the desired target structure of the compound of the invention.

In a second variant, by the procedure of the invention, it is possible first to prepare an intermediate containing the central group I and four spacer groups from the compounds III, especially the tetrols III, and an appropriate organic compound. The appropriate organic compound is chosen so that the resulting spacer groups each carry one reactive functional group. In a second stage, these reactive functional groups are reacted with a suitable organic compound to form the reactive functional groups II and thus the compounds of the invention. In accordance with the invention, preference is given to this variant.

Examples of suitable organic compounds are the compounds listed above in connection with the first variant.

Examples of suitable reactive functional groups are the functional groups listed above in connection with the first variant.

Examples of organic compounds which are suitable for this variant are epsilon-caprolactone, hexahydro-phthalic acid, hexahydrophthalic anhydride, phthalic acid, phthalic anhydride, hexahydroterephthalic acid, terephthalic acid, fumaric acid, maleic acid, maleic anhydride, itaconic acid, itaconic anhydride, oxalic acid, malonic acid, malonic anhydride, succinic acid, succinic anhydride, glutaric acid, glutaric anhydride, adipic acid, adipic anhydride, pimelic acid, suberic acid, azelaic acid, sebacic acid or decane-, undecane- or dodecanedicarboxylic acid. Of these, epsilon-caprolactone, maleic acid or maleic anhydride and hexahydrophthalic anhydride are especially suitable and are therefore used with particular preference in accordance with the invention.

Examples of highly suitable organic compounds which may be reacted in the second stage with the intermediate to form the reactive functional groups II and thus the compounds of the invention are compounds containing epoxide groups, especially compounds containing glycidyl groups.

Examples of suitable compounds containing epoxide groups, especially compounds containing glycidyl groups, are ethylene oxide, propylene oxide, epichlorohydrin, glycidol, glycidyl ethers, especially aryl and alkyl glycidyl ethers, or glycidyl esters, especially the glycidyl esters of tertiary, highly branched, saturated monocarboxylic acids, which are sold under the trade name Versatic$^R$ acids by the company Deutsche Shell Chemie. Of these, the Versatic$^R$ acid glycidyl esters, which are sold under the trade name Cardura$^R$ E10, are especially advantageous and are therefore used with very particular preference.

Further examples of highly suitable organic compounds which may be reacted in the second stage with the intermediate to form the reactive functional groups II and thus the compounds of the invention are acrylic acid and methacrylic acid.

All variants of the process of the invention may be conducted in solution or in bulk. Depending on the reactants present, it is possible to operate under pressure. In general, the appropriate reaction temperatures are from −50 to +300° C., preferably from 0 to 250° C., more preferably from room temperature to 200° C. and in particular from 60 to 160° C. The reaction conditions that are particularly suitable in each case may easily be selected by the skilled worker on the basis of the properties of the reactants.

The compounds of the invention, especially those prepared in the manner of the process of the invention, have particular advantages. In numerous end uses they are superior to the known hyperbranched compounds and dendrimers, so that they may be used very much more widely than the latter.

For instance, they permit the preparation of new dendrimers of higher generations in a simple way.

In particular, the compounds of the invention make it possible, very generally, to prepare multisubstance mixtures of the invention which are liquid, solid or dispersed or dissolved in aqueous or organic media, and which have new advantageous profiles and performance properties. For instance, the compounds of the invention are used to obtain sealing compounds, adhesives or coating compositions, in dispersion or solution in aqueous or organic media, which have particularly high solids contents. Furthermore, powder coating materials and powder slurries of the invention possess advantageously low film formation temperatures, which are not too close to the crosslinking temperature. Additionally, the coating compositions of the invention are suitable for the production of films, especially self-supporting paint films.

The coating compositions, adhesives and sealing compounds of the invention may be air drying, physically drying, thermally curable, curable with actinic light, and/or curable with electron beams. In this context, the thermally curable coating compositions, adhesives and sealing compounds of the invention have particular advantages.

The coating compositions of the invention may comprise
  in solution or dispersion in aqueous or organic media
  spray coating materials, liquid coating materials, powder coating materials or powder slurries. These are outstandingly suitable for all end uses to which coating materials are commonly put. In particular, they are suitable as coating materials for the industrial sector, furniture coatings, architectural coatings, automotive OEM coating materials, or automotive refinish coating materials.

Very particular advantages are possessed by the coating compositions of the invention comprising compounds of the invention containing hydroxyl groups as reactive functional groups II.

Besides the compounds of the invention, the coating compositions of the invention, of the type specified above, comprise binders which likewise contain hydroxyl groups.

Suitable hydroxy-functional binders are preferably binders based on polyacrylates, polyesters, polyurethanes, acrylated polyurethanes, acrylated polyesters, polylactones, polycarbonates, polyethers and/or (meth)acrylatediols. Hydroxy-functional binders are known to the skilled worker, and numerous suitable examples are available commercially.

Preference is given to the use of polyacrylates, polyesters and/or polyurethanes. Examples of binders of this kind that are used with particular preference are:

1. Polyacrylates having a hydroxyl number of from 40 to 240, preferably from 60 to 210, in particular from 100 to 200, an acid number of from 0 to 35, glass transition temperatures of from −35 to 85° C., and number-average molecular weights $M_n$ of from 1 500 to 300 000.

The glass transition temperature of the polyacrylates is determined, as is known, by the nature and amount of the monomers used. The selection of the monomers may be made by the skilled worker with assistance from the following formula V, by which the glass transition temperatures may be calculated approximately.

$$1/Tg = \sum_{n=1}^{n=x} W_n/Tg_n; \sum_n W_n = 1 \quad (V)$$

Tg=Glass transition temperature of the polyacrylate resin
   $W_n$=Weight fraction of the nth monomer
   $Tg_n$=Glass transition temperature of the homopolymer of the nth monomer
   x=Number of different monomers Measures to control the molecular weight (e.g., selection of appropriate polymerization initiators, use of chain transfer agents or of special techniques of polymerization, etc.) belong to the art and need not be elucidated in any more detail here.

1.1 Particularly preferred polyacrylates are preparable by polymerizing (a1) from 10 to 92, preferably from 20 to 60% by weight of an alkyl or cycloalkyl methacrylate having 1 to 18, preferably 4 to 13, carbon atoms in the alkyl or cycloalkyl radical, or mixtures of such monomers, (a2) from 8 to 60, preferably from 12.5 to 50.0% by weight of a hydroxyalkyl acrylate or hydroxyalkyl methacrylate having 2 to 4 carbon atoms in the hydroxyalkyl radical, or mixtures of such monomers, (a3) from 0 to 5, preferably from 0.7 to 3% by weight of acrylic acid or methacrylic acid or mixtures of these monomers and (a4) from 0 to 50, preferably up to 30% by weight, of ethylenically unsaturated monomers different than but copolymerizable with (a1), (a2) and (a3), or mixtures of such monomers, (a4), to give polyacrylates of the specification indicated above.

Examples of suitable (a1) components are methyl, ethyl, propyl, n-butyl, isobutyl, tert-butyl, pentyl, hexyl, heptyl or 2-ethylhexyl acrylate or methacrylate and also cyclohexyl, tert-butyl-cyclohexyl or isobornyl acrylate or methacrylate.

Examples of suitable (a2) components are hydroxyethyl, hydroxypropyl or hydroxybutyl or hydroxy-methylcyclohexyl acrylate or methacrylate or adducts of (meth)acrylic acid and epoxides such as Versatic acidR glycidyl esters.

Example of suitable (a4) components are vinylaromatics such as styrene, vinyltoluene, alpha-methylstyrene, alpha-ethylstyrene, ring-substituted diethylstyrenes, isopropylstyrene, butylstyrene and methoxystyrenes; vinyl ethers such as ethyl vinyl ether, n-propyl vinyl ether, isopropyl vinyl ether, n-butyl vinyl ether or isobutyl vinyl ether; vinyl esters such as vinyl acetate, vinyl propionate, vinyl butyrate, vinyl pivalate or the vinyl ester of 2-methyl-2-ethylheptanoic acid; or allyl ethers such as trimethylolpropane monoallyl, diallyl or triallyl ether or ethoxylated or propoxylated allyl alcohol.

1.2 Further examples of particularly preferred polyacrylates are described in the European patent application EP-A-0 767 185 and in the American patents U.S. Pat. No. 5,480,493, 5,475,073 or 5,534,598.

1.3 Further examples of particularly preferred polyacrylates are sold under the brand name Joncryl$^R$, such as Joncryl$^R$ SCX 912 and 922,5, for instance.

1.4 Further examples of particularly preferred polyacrylates are those obtainable by polymerizing (a1) from 10 to 51% by weight, preferably from 25 to 41% by weight, of 4-hydroxy-n-butyl acrylate or methacrylate or a mixture thereof, but especially 4-hydroxy-n-butyl acrylate, (a2) from 0 to 36% by weight, preferably from 0.1 to 20% by weight, of a non-(a1) hydroxyl-containing ester of acrylic acid or of methacrylic acid, or a mixture thereof, (a3) from 28 to 85% by weight, preferably from 40 to 70% by weight, of an aliphatic or cycloaliphatic ester of methacrylic acid having at least four carbon atoms in the alcohol residue and being different than (a1) and (a2), or a mixture of such monomers (a3), (a4) from 0 to 3% by weight, preferably from 0.1 to 2% by weight, of an ethylenically unsaturated carboxylic acid or a mixture of such acids, and (a5) from 0 to 20% by weight, preferably from 5 to 15% by weight, of an unsaturated monomer different than (a1), (a3) and (a4), or a mixture of such monomers (a5), to give a polyacrylate having a hydroxyl number of from 60 to 200, preferably from 100 to 160, an acid number of from 0 to 35 and a number-average molecular weight Mn of from 1 500 to 10 000, the composition of component (a3) being chosen so that polymerization of this component (a3) alone gives a polymethacrylate having a glass transition temperature of from +10 to +100° C., preferably from +20 to +60° C.

Examples of suitable components (a2) are hydroxyalkyl esters of acrylic acid and methacrylic acid such as hydroxyethyl or hydroxypropyl acrylate or methacrylate, the choice being made such that polymerization of this component (a2) alone gives a polyacrylate having a glass transition temperature of from 0 to +80° C., preferably from +20 to +60° C.

Examples of suitable components (a3) are aliphatic esters of methacrylic acid having 4 to 20 carbon atoms in the alcohol residue, such as n-butyl, isobutyl, tert-butyl, 2-ethylhexyl, stearyl and lauryl methacrylate; or cycloaliphatic esters of methacrylic acid such as cyclohexyl methacrylate. Examples of suitable components (a4) are acrylic acid and/or methacrylic acid.

Examples of suitable components (a5) are vinylaromatic hydrocarbons such as styrene, alpha-alkylstyrene or vinyltoluene; amides of acrylic acid and methacrylic acid such as methacrylamide and acrylamide; nitrites of acrylic acid and methacrylic acid; vinyl ethers or vinyl esters, the composition of this component (a5) preferably being such that polymerization of components (a5) alone results in a polyacrylate having a glass transition temperature of from +70 to +120° C., in particular from +80 to +100° C.

1.5 The preparation of these polyacrylates is common knowledge and is described, for example, in the standard work Houben-Weyl, Methoden der organischen Chemie, 4th edition, volume 14/1, pages 24 to 255, 1961.

2. Polyester resins preparable by reacting (a1) at least one cycloaliphatic or aliphatic polycarboxylic acid, (a2) at least one aliphatic or cycloaliphatic polyol having more than two hydroxyl groups in the molecule, (a3) at least one aliphatic or cycloaliphatic diol, and (a4) at least one aliphatic, linear or branched saturated monocarboxylic acid, in a molar ratio of (a1):

(a2): (a3): (a4)=1.0: 0.2 to 1.3: 0.0 to 1.1: 0.0 to 1.4, preferably 1.0: 0.5 to 1.2: 0.0 to 0.6: 0.2 to 0.9, to give a polyester or alkyd resin.

Examples of suitable components (a1) are hexahydrophthalic acid, 1,4-cyclohexane-dicarboxylic acid, endomethylenetetrahydrophthalic acid, oxalic acid, malonic acid, succinic acid, glutaric acid, adipic acid, pimelic acid, suberic acid, azelaic acid or sebacic acid.

Examples of suitable components (a2) are pentaerythritol, trimethylolpropane, triethylolethane and glycerol.

Examples of suitable components (a3) are ethylene glycol, diethylene glycol, propylene glycol, neopentyl glycol, 2-methyl-2-propyl-1,3-propane-diol, 2-methyl-2-butyl-1,3-propanediol, 2,2,4-tri-methyl-1,5-pentanediol, 2,2,5-trimethyl-1,6-hexanediol, neopentyl glycol hydroxypivalate or dimethylolcyclohexane.

Examples of suitable components (a4) are 2-ethylhexanoic acid, lauric acid, isooctanoic acid, isononanoic acid or monocarboxylic acid mixtures obtained from coconut oil or palm kernel oil.

The preparation of the polyesters and alkyd resins used with preference in accordance with the invention is common knowledge and is described, for example, in the standard work Ullmanns Enklopädie der technischen Chemie, 3rd Edition, volume 14, Urban & Schwarzenberg, Munich, Berlin, 1963, pages 80 to 89 and pages 99 to 105, and also in the following books: "Résines Alkydes-Polysters" by J. Bourry, Paris, Dunod, 1952, "Alkyd Resins" by C. R. Martens, Reinhold Publishing Corporation, New York, 1961, and "Alkyd Resin Technology" by T. C. Patton, Interscience Publishers, 1962.

3. Polyurethanes as described in the patents EP-A-0 708 788, DE-A-44 01 544 or DE-A-195 34 361.

To further increase the solids content, a portion of the binders may be replaced by reactive diluents. Examples of suitable reactive diluents are branched, cyclic and/or acyclic $C_9$–$C16$ alkanes functionalized with at least two hydroxyl or thiol groups or at least one hydroxyl and at least one thiol group, especially diethyloctanediols.

Further examples of suitable reactive diluents are oligomeric polyols obtainable from oligomers, which are obtained by metathesis reactions of acyclic monoolefins and cyclic monoolefins, by hydroformylation and subsequent hydrogenation; examples of suitable cyclic monoolefins are cyclobutene, cyclopentene, cyclohexene, cyclooctene, cycloheptene, norbornene or 7-oxa-norbornene; examples of suitable acyclic monoolefins are present in hydrocarbon mixtures which are obtained in petroleum processing by cracking ($C_5$ cut); examples of suitable oligomeric polyols for use in accordance with the invention have a hydroxyl number (OHN) of from 200 to 450, a number-average molecular weight $M_n$ of from 400 to 1 000 and a mass-average molecular weight $M_w$ of 600 to 1 100;

Furthermore, the coating compositions of the invention comprise crosslinkers, which enter into crosslinking reactions with the hydroxyl groups in the compounds of the invention and in the binders and also, if appropriate, in the reactive diluents.

Resins suitable for this purpose are the customary and known amino resins whose methylol and/or methoxymethyl groups may have been partly defunctionalized by means of carbamate or allophanate groups. Crosslinkers of this kind are described in the patents U.S. Pat. No. 4,710,542 and EP-B-0 245 700 and also in the article by B. Singh and coworkers, "Carbamylmethylated Melamines, Novel Crosslinkers for the Coatings Industry" in Advanced Organic Coatings Science and Technology Series, 1991, volume 13, pages 193 to 207.

Besides these crosslinkers, further crosslinkers may also be present. Examples of suitable further crosslinkers are resins or compounds containing siloxane groups, resins or compounds containing anhydride groups, resins or compounds containing epoxide groups, blocked and/or unblocked, monomeric and/or oligomeric polyisocyanates, and/or tris(alkoxy-carbonylamino)triazines, as are described in the patents U.S. Pat. No. 4,939,213, U.S. Pat. No. 5,084,541, U.S. Pat. No. 5,288,865 or EP-A-0 604 922.

The viscosity of the crosslinkers is generally between 10 and 20 000 mPas. Its functionality is normally between 1 and 5, in particular 1.5 and 4.5.

Depending on the reactivity of the further crosslinker, it may be added directly to the coating compositions of the invention to give what is known as a one-component system. If it is a particularly reactive crosslinker, such as a polyisocyanate or an epoxide, it is generally not added to the coating compositions of the invention until shortly before use. This results in what is known as a two-component or multicomponent system, as are known in particular from the automotive refinish sector.

The coating compositions of the invention may comprise customary and known additives in customary and known, effective amounts.

Examples of suitable additives are polymers, crosslinkers, crosslinking catalysts, initiators, especially photoinitiators, pigments, dyes, fillers, reinforcing fillers, rheological assistants, solvents, wetting agents, dispersants, defoamers, adhesion promoters, additives for improving substrate wetting, additives for improving surface smoothness, flatting agents, leveling agents, film forming auxiliaries, dryers, antiskimming agents, light stabilizers, corrosion inhibitors, biocides, flame retardants, polymerization inhibitors, especially photoinhibitors, or plasticizers, as are customary and known, for example, in the plastics or coatings sector.

The selection of the additives is guided by the desired profile of properties of the coating compositions, adhesives and sealing compounds of the invention and by their specific end uses and may therefore be made by the skilled worker in a simple manner, possibly with the assistance of simple preliminary tests.

EXAMPLES

Example 1

Preparation of an Inventive Compound

A 4 l steel reactor was charged with 128 g of homopentaerythritol and 462 g of hexahydrophthalic anhydride and this initial charge was heated at 120° C. for four hours. Subsequently, 729.6 g of Versatic$^R$ acid glycidyl ester were added and heating was continued until an acid number of 6.6 was reached. The resulting inventive compound was diluted with butyl acetate at 90° C. to give a solids content of 85% by weight. The number-average molecular weight Mn of the inventive compound was 1 430, its mass-average molecular weight Mw 1 865.

For the purpose of comparing the viscosity values, a dilution curve was drawn up. For this purpose, the solids content of the original sample was gradually lowered using butyl acetate, and the viscosity of the resulting solutions was measured using a cone-and-plate viscometer. The results obtained are given in Table 1.

TABLE 1

The viscosities of the inventive compound at different concentrations

| Solids content (% by weight) | Viscosity (dPa · s) |
|---|---|
| 85 | 131.2 |
| 80.4 | 27.2 |
| 74.8 | 7.7 |
| 69.6 | 2.3 |
| 64.4 | 0.9 |

Comparative Experiment C1

Preparation of an Noninventive Hyperbranched Compound

A 4 l steel reactor was charged with 134 g of trimethylolpropane and 462 g of hexahydrophthalic anhydride and this initial charge was heated at 120° C. for 6.5 hours. Subsequently, 684 g of Versatic$^R$ acid glycidyl ester were added and heating was continued until an acid number of 4.5 was reached. The resulting hyperbranched compound C1 was diluted with butyl acetate at 90° C. to give a solids content of 84.4% by weight. The number-average molecular weight Mn of the hyperbranched compound C1 was 1 499, its mass-average molecular weight Mw 2 485.

For the purpose of comparing the viscosity values, a dilution curve was drawn up. For this purpose, the solids content of the original sample was lowered using butyl acetate, and the viscosity of the resulting solutions was measured using a cone-and-plate viscometer. The results obtained are given in Table 2.

TABLE 2

The viscosities of the hyperbranched compound C1 at different concentrations

| Solids content (% by weight) | Viscosity (dPa · s) |
|---|---|
| 78.7 | 33.6 |
| 75.5 | 9 |
| 70.0 | 3.4 |
| 64.8 | 1.2 |
| 60.0 | 0.4 |

Comparative Experiment C2

Preparation of an Noninventive Hyperbranched Compound C2

A 4 l steel reactor was charged with 136 g of pentaerythritol and 616 g of hexahydrophthalic anhydride and this initial charge was heated at 150° C. for 6.5 hours. Subsequently, 904 g of Versatic$^R$ acid glycidyl ester were added and heating was continued until an acid number of 0.7 was reached. The resulting hyperbranched compound C2 was diluted with butyl acetate at 90° C. to give a solids content of 83.2% by weight. The number-average molecular weight Mn of the hyperbranched compound C2 was 1 684, its mass-average molecular weight Mw 3 280.

For the purpose of comparing the viscosity values, a dilution curve was drawn up. For this purpose, the solids content of the original sample was lowered using butyl acetate, and the viscosity of the resulting solutions was measured using a cone-and-plate viscometer. The results obtained are given in Table 3.

TABLE 3

The viscosities of the hyperbranched compound C2 at different concentrations

| Solids content (% by weight) | Viscosity (dPa · s) |
|---|---|
| 83.2 | 192.0 |
| 80.4 | 66.4 |
| 75.2 | 16.4 |
| 70.1 | 4.8 |
| 65.0 | 1.7 |

The comparison of the results of Tables 1 to 3 demonstrates that, above a solids content of 75% by weight, the inventive compound exhibits significantly lower viscosities than the hyperbranched compounds C1 and C2, which in performance terms is a particular advantage.

Example 2 and Comparative Experiments C3 and C4

The Effect of the Inventive Compound from Example 1 and of the Hyperbranched Compounds C1 and C2 from Comparative Experiments C1 and C2 on the Viscosity of Binder Solutions Mixtures of the polyacrylate (binder) as described in Example E1 of the German Laid-Open Specification DE-A-44 07 415, and of the inventive compound and the hyperbranched compound C1 and C2 were prepared, in each case in a ratio of 1:1.

In Example 2, the polyacrylate E1 and the inventive compound from Example 1 were mixed with one another.

In the Comparative Experiment C3, the polyacrylate E1 was mixed with the hyperbranched compound C1 from Comparative Experiment C1, and, in the Comparative Experiment C4, the polyacrylate E1 was mixed with the hyperbranched compound C2 from Comparative Experiment C2.

Said polyacrylate contains the following monomers copolymerized in the stated amounts: styrene (23% by weight), n-butyl methacrylate (6% by weight), t-butyl-cyclohexyl acrylate (14% by weight), methyl methacrylate (21% by weight) and also a mixture of—based on the mixture—25% by weight of 3-hydroxy-n-propyl methacrylate and 75% by weight of 2-hydroxy-n-propyl methacrylate (36% by weight).

The resulting mixtures were adjusted to different solids contents using butyl acetate. For comparison, solutions of the polyacrylate E1 in butyl acetate with different solid contents were employed. The viscosities of the resulting solutions were determined using a cone-and-plate viscometer. The results of the experiment are given in Table 4.

TABLE 4

The effect of the inventive compound from Example 1 and the hyperbranched compounds C1 and C2 from Comparative Experiments C1 and C2 on the viscosity of binder solutions

|  | Solids content (% by weight) | Viscosity (dPa · s) |
|---|---|---|
| Polyacrylate E1 | 63.2 | 65.6 |
|  | 62.5 | 58.4 |
| Example 2 | 71.3 | 54.4 |
|  | 64.5 | 5.1 |
| Comparative Experiment C3 | 70.1 | 34.0 |
|  | 59.4 | 2.6 |
| Comparative Experiment C4 | 71.6 | 76.8 |
|  | 62.8 | 6.2 |

The comparison shows that the inventive compound results in a comparatively low viscosity at high solids contents.

Example 3 and Comparative Experiments C5 and C6

Preparation of an Inventive Coating Composition from the Mixture from Example 2 and of Noninventive Coating Compositions from the Mixtures from Comparative Experiments C3 and C4

For the preparation of the inventive coating composition (=Example 3), 42.5 parts of the mixture from Example 2 (solids content: 71.3% by weight) were admixed with 18.45 parts of Desmodur$^R$ VPLS 2025 (blocked polyisocyanate based on hexamethylene diisocyanate from Bayer AG), 0.1 part of a 10% strength solution of dibutyltin dilaurate in butyl acetate and 2.05 parts of butyl acetate. The viscosity of the resulting coating material is 17.4 dPas.

For the Comparative Experiment C5, 35.1 parts of the mixture from Comparative Experiment C3 (solids content: 70.1% by weight) were admixed with 16.89 parts of a mixture of 15.11 parts of Desmodur$^R$ VPLS 2025, 0.1 part of a 10% strength solution of dibutyltin dilaurate in butyl acetate and 1.68 parts of butyl acetate. The viscosity of the resulting coating material is 13.0 dpas.

For the Comparative Experiment C6, 35.8 parts of the mixture from Comparative Experiment C4 (solids content: 71.6% by weight) were admixed with 15.72 parts of a mixture of 14.06 parts of Desmodur$^R$ VPLS 2025, 0.1 part of a 10% strength solution of dibutyltin dilaurate in butyl acetate and 1.56 parts of butyl acetate. The viscosity of the resulting coating material is 22.4 dpas.

The coating materials of Example 3 and of the Comparative Experiments C5 and C6 were knife coated onto glass plates to give a wet film thickness of 150 micrometers, and were baked at 60° C. and 130° C. for one hour in each case. The hardness of the resultant coatings was determined with the aid of the pendulum attenuation test in accordance with DIN 53157. The results are given in Table 5.

TABLE 5

The pendulum attenuation of the coatings from Example 3 and from the Comparative Experiments C5 and C6

|  | Pendulum attenuation (s) |
|---|---|
| Example 3 - Curing temperature: |  |
| 60° C. | 93.8 |
| 130° C. | 197.4 |
| Comparative Experiment C5 - Curing temperature: |  |
| 60° C. | 50.4 |
| 130° C. | 187.6 |
| Comparative Experiment C6 - Curing temperature |  |
| 60° C. | 88.2 |
| 130° C. | 200.2 |

The comparison of the respective pendulum attenuations shows that the inventive coating composition of Example 3, based on the inventive compound from Example 1, gives—at a significantly lower viscosity—an inventive coating which has the same hardness as the coatings based on the noninventive coating compositions from Comparative Experiments C5 and C6.

What is claimed is:

1. A hyperbranched compound having a tetrafunctional central group of the general formula I

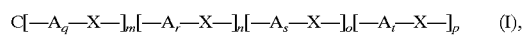

in which the indices and variables have the following meanings:

$m+n+o+p=4$; where m=an integer from 1 to 3 and n, o and p=0 or an integer from 1 to 3;

q, r, s and t=an integer from 1 to 5, where q>r, s, t;

X=—O—, —S— or —NH—;

A=—CR$_2$—; where
   R=—H, —F, —Cl, —Br, —CN, —NO$_2$, C$_1$–C$_3$ alkyl or C$_1$–C$_3$ haloalkyl or C$_1$–C$_3$ alkoxy radical or,
   if q, r, s and/or t=at least 2, a C$_2$–C$_4$ alkanediyl and/or C$_2$–C$_4$ oxaalkane-diyl radical which cyclically bridges 2 to 5 carbon atoms, and/or an oxygen atom —O—, which cyclically bridges 3 to 5 carbon atoms, of the radical —A—.

2. The hyperbranched compound as claimed in claim 1, wherein the central group I is connected to one reactive functional group in each case via spacer groups.

3. The hyperbranched compound as claimed in claim 1, wherein the reactive functional group comprises a group of the general formula II

in which the indices and variables have the following meanings:

X=—O—, —S— or —NH—;

B=—H, —Z or —R$^1$—(—Z$^1$)$_u$ where u=1 or 2 and
   Z=—C(O)—NH$_2$,
   —C(O)—NH—C(O)—NH$_2$,
   —C(O)—OR$^2$,

—C(O)—NH—C(O)—OR², 
—C(O)—CH₂—C(O)—R², 
—O—C(O)—CH₂—C(O)—R², 
C(O)—CR³=CH₂,

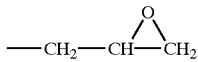

—Si—(OR⁴)₃, 
—(—CH₂—)ᵥ—CH=CH₂, 
—C(O)—(—CH₂—)ᵥ—CH=CH₂, in which the index v is 0 or is an integer from 1 to 3, 
—C(O)—CH=CH—C(O)—O—R², 
—C(O)—CH=CH—CH=CH—R², or 
—C(O)—CH=CH—CH₂—CH=CH—R²; 
Z¹=—OH, —NH₂, —SH, 
—COOH, —SO₃H, —PO₃H, 
—O—C(O)—NH₂, 
—O—C(O)—NH—C(O)—NH₂, 
—NCO, 
—NH—C(O)—OR², 
—NH—C(O)—NH—C(O)—OR², 
—O—C(O)—CH₂—C(O)—R², 
—O—C(O)—CH₂—C(O)—OR², 
—O—C(O)—CR³=CH₂,

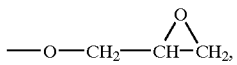

—O—Si—(OR⁴)₃, 
—O—(—CH₂—)ᵥ—CH=CH₂, 
—O—C(O)—(—CH₂—)ᵥ—CH=CH₂, in which the index v is 0 or an integer from 1 to 3, 
—O—C(O)—CH=CH—C(O)—O—R², 
—O—C(O)—CH=CH—CH=CH—R², or 
—O—C(O)—CH=CH—CH₂—CH=CH—R²; 
where 
R²=unsubstituted or substituted C₁–C₁₀ alkyl, C₅–C₁₀ cycloalkyl, C₆–C₂₀ cycloalkylalkyl, C₆–C₂₀ alkylcycloalkyl, C₆–C₁₀ aryl, C₇–C₂₀ arylalkyl, C₇–C₂₀ alkylaryl, C₁₁–C₂₆ arylcycloalkyl, or C₁₁–C₂₆ cycloalkylaryl radical, the alkyl radical being branched or unbranched; 
R³ =C₁–C₄ alkyl radical or —CN; 
R⁴ =unsubstituted or substituted C₁–C₄ alkyl radical or phenyl radical; 
R¹ =divalent or trivalent radical derived from 
(i) an alkane, alkene, cycloalkane, cycloalkene, alkylcycloalkane, alkylcycloalkene, alkenylcycloalkane, or alkenylcycloalkene, an aromatic, heteroaromatic, or an alkyl-, alkenyl-, cycloalkyl-, cycloalkenyl-, alkylcycloalkyl-, alkylcycloalkenyl-, alkenylcycloalkyl- or alkenylcycloalkenyl- substituted aromatic or heteroaromatic compound; or 
ii) a radical mentioned under (i) which contains at least one heteroatom in the chain and/or in the ring; or 
(iii) a radical mentioned under (i) or (ii) whose chain and/or ring is substituted.

4. A process for preparing a dendrimeric compound, comprising a step of reacting a hyperbranched compound as claimed in claim 1 to prepare a dendrimeric compound of higher generation.

5. A multisubstance mixture which comprises a hyperbranched compound as claimed in claim 1.

6. A dendrimeric compound which comprises as central group a hyperbranched compound as claimed in claim 1.

7. The multisubstance mixture of claim 5, which is a coating composition, adhesive or sealing compound.

8. A multisubstantce mixture as claimed in claim 7, which is air-drying, physically drying, thermally curable, curable with actinic light or curable with electron beams.

9. A multisubstance mixture as claimed in claim 7, wherein the multisubstance mixture is a coating composition comprising—dissolved or dispersed in aqueous or organic media—a spray coating material, liquid coating material, powder coating material or powder slurry.

10. A multisubstance mixture as claimed in claim 7, wherein the multisubstance mixture is a coating composition for the industrial sector or a furniture coating, architectural coating, automotive OEM coating, or automotive refinish coating material.

11. The hyperbranched compound as claimed in claim 3, wherein Z=—C(O)—(—CH₂—)ᵥ—CH=CH₂ and/or Z¹=—O—C(O)—(—CH₂—)ᵥ—CH=CH₂, in which the index v is 0 or 1.

12. The hyperbranched compound as claimed in claim 3, wherein the central group I is connected to one reactive functional group in each case via spacer groups.

13. A multisubstance mixture which comprises a hyperbranched compound as claimed in claim 2.

14. A multisubstance mixture which comprises a hyperbranched compound as claimed in claim 3.

15. A dendrimeric compound which comprises as central group a hyperbranched compound as claimed in claim 2.

16. A dendrimeric compound which comprises as central group a hyperbranched compound as claimed in claim 3.

17. A multisubstance mixture as claimed in claim 8, wherein the multisubstance mixture is a coating composition comprising—dissolved or dispersed in aqueous or organic media—a spray coating material, liquid coating material, powder coating material or powder slurry.

18. A multisubstance mixture as claimed in claim 8, wherein the multisubstance mixture is a coating composition for the industrial sector or a furniture coating, architectural coating, automotive OEM coating, or automotive refinish coating material.

19. A multisubstance mixture as claimed in claim 9, wherein the multisubstance mixture is a coating composition for the industrial sector or a furniture coating, architectural coating, automotive OEM coating, or automotive refinish coating material.

* * * * *